United States Patent
Weng et al.

(10) Patent No.: US 7,820,430 B2
(45) Date of Patent: Oct. 26, 2010

(54) MICRO DEVICE FOR CELL CULTURE

(75) Inventors: Yu-Shi Weng, Pingtung (TW);
Ming-Cheng Shih, Taichung (TW);
Rung-Jiun Gau, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 1082 days.

(21) Appl. No.: 11/503,123

(22) Filed: Aug. 14, 2006

(65) Prior Publication Data

US 2007/0122897 A1    May 31, 2007

(30) Foreign Application Priority Data

Nov. 28, 2005    (TW) ............... 94141732 A

(51) Int. Cl.
*C12M 3/00*    (2006.01)
(52) U.S. Cl. .............. 435/293.1; 435/288.5; 435/293.2; 435/294.1; 435/305.3; 422/130
(58) Field of Classification Search .............. 435/288.5, 435/293.1, 293.2, 294.1, 305.2; 422/130
See application file for complete search history.

(56) References Cited

U.S. PATENT DOCUMENTS 6,197,575 B1 * 3/2001 Griffith et al. ............ 435/288.4
7,029,907 B2    4/2006 Li et al. .................... 435/297.1
2002/0173033 A1 * 11/2002 Hammerick et al. ...... 435/305.2
2005/0260745 A1    11/2005 Domansky et al.

OTHER PUBLICATIONS

Ming-Cheng Shih et al., "A Novel Micro-Tissue Reactor for Maintaining Hepatocytes in Vitro", essay in 4 pages.

* cited by examiner

*Primary Examiner*—William H Beisner
(74) *Attorney, Agent, or Firm*—Bacon & Thomas, PLLC

(57) ABSTRACT

A micro device for cell culture is disclosed, which cooperates with a fluid and includes: a top plate having an inlet port; a orifice plate having a plurality of orifices; a culture plate having a plurality of culture wells and a plurality of injection ports; and a bottom plate having at least one collecting well and at least one collecting flow channel, wherein, the culture plate is placed between the orifice plate and the bottom plate. The collecting flow channel connects to all regulating orifices in the culture wells and guides the fluid from the culture wells, then receives the fluid in the collecting well. The fluid flows into the orifice plate from the inlet port of the top plate, and then diversifies into the culture plate, then arrives at each culture well by way of the injection ports, and finally collects in the collecting well of the bottom plate.

25 Claims, 12 Drawing Sheets

MICRO DEVICE FOR CELL CULTURE

BACKGROUND OF THE INVENTION

1. Field of the Invention

The present invention relates to a micro device for cell culture and, more particularly, to a micro device combining control systems that provide gradient formation of bio-molecules which imitates the physical tissue environment in vivo while culturing cells in vitro.

2. Description of Related Art

Cell culture techniques are basic in vitro tools used for studying varies biological or biomedical phenomena. During early stage of drug development, for example, cell culture techniques are frequently used to predict the metabolism and toxicology of drug candidates, or xenobiotics, instead of animal model experiments. The advantage of cell culture model is convenient and can used for speeding up the screening process.

Generally, current cell culture methods can be classified into several groups: (1) conventional culture without fluidic environments, (2) fluidic culture with single-direction laminar flow. (3) cell culture on 3-D scaffold composed of biomaterials or extra-cellular matrix. Limitation of conventional static culture includes lack of mass transformation system of bimolecular and appropriate micro-architecture. As for single-direction laminar flow, which unable to provide more sophisticated fluidic pattern or gradient formation of bio-molecules that imitate physiological environment in vivo. In summary, a reliable model to represent the physical activities of cells is still required for most predictive study of drug or xenobiotic metabolism and toxicity.

A good in vitro model is pivotal to discover the potential of drug candidates as well as to predict xenobiotic metabolism for the studies of environmental toxicology. A cell culture system with micro-architecture cell culture unit which imitating the physical environment, three-dimensional fluidic pattern and dynamic fluidic control system will provide promising platform for predictive study during drug development in vitro.

SUMMARY OF THE INVENTION

The object of the present invention is to provide a micro device for culturing tissue-specific cells. The micro device of the present invention provides incubating conditions that imitate the physical environment in vivo. Further, the advantages of the present invention are to control the cytokines secretion by control of concentration gradient that mimic microenviroment of liver tissue, create opportunities for cell interaction between different types of cells, hepatocytes and non parenchymal cells, for example. In addition to function as a single culture device, the micro device can be further produced in batches format by disposable materials at low cost, to provide a personal medical device with great benefit.

The present invention provides a method for generating pressure and concentration gradients in a cell culture well, comprising introduces a radially-inward fluid or fluids from discrete injection ports on the peripheral of the culture well, and the radially-inward fluid flows toward the central regulating orifices of the culture well to generate pressure and concentration gradients. The term of fluid used in the specification includes liquid or gas or both.

The present invention also provides a micro device for cell culture, comprising one or more culture wells; a plurality of discrete injection ports on the peripheral of the culture wells; one or more regulating orifices on the wall of the culture wells; wherein a fluid or fluids were introduced from the discrete injection ports and the fluid(s) radially-inward flow toward the one or more regulating orifices on the wall of the culture wells.

The micro device for cell culture of the invention cooperates with a fluid and includes: a top plate having an inlet port; a culture plate having one or more culture wells and one or more injection ports which are able to form a specific fluidic pattern with gradient of nutrients, bimolecular, for example, through a programmed control system connect culture wells with at least one regulating orifice to drain the fluids from the culture wells; and a bottom plate having at least one flow channel.

Another embodiment of the micro device for cell culture of the present invention includes: a top plate having at least one inlet port; a orifice plate having a plurality of orifices; a culture plate with a plurality of culture wells and a plurality of injection ports formed on one surface of the culture plate. The injection ports connect the culture wells and orifices on the orifice plate, and the culture wells contain at least one regulating orifice to drain the fluids from the culture wells. A bottom plate has at least one collecting well and at least one flow channel. The culture plate is fixed between the orifice plate and the bottom plate in assembly. The flow channels connect to all regulating orifices in the culture wells, and guide the fluids from the culture wells to the collecting well. Furthermore, the flow channels on the bottom plate can be the collecting well.

In the micro device for cell culture of the invention, the fluid flows into the orifice plate from the inlet port, diversifies into a plurality of culture plates via injection ports, and finally arrives at the collecting well of the bottom plate.

In this invention, the flow channels and the collecting well can be formed on the surface of the bottom plate which faces the culture plate. Alternatively, the flow channels and the collecting well can be formed on the surface of the culture plate which faces the bottom plate, and the flow channels and the collecting well will be formed when the culture plate is assembled with the bottom plate.

The collecting well on the bottom plate can be directly connected with an outlet port in order to drain out the fluid from the collecting well. Alternatively, outlet ports can be defined in the top plate, orifice plate, and culture plate. While assembling the components, each outlet port and the collecting well on the bottom plate are connected so that back-flow of the fluid from the collecting well to the top plate and drain out from the outlet ports on the top plate is facilitated. As a result, the fluid in the collecting well on the bottom plate is circulated, and the objective of full utilization is achieved.

In the micro device for cell culture of the invention, a buffer zone is formed to temporarily reserve the fluid from the top plate when connecting the top plate with the orifice plate. This buffer zone can be either on the top plate facing one surface of the orifice plate, or on the orifice plate facing one side of the top plate.

The utility of the orifice plate of the present invention depends on requirements, and there is no limitation for the structure of the orifice plate. A better result can be achieved when a plurality of orifices is formed, and each orifice connects with the injection ports and the buffer zone area which is formed when the top plate and the orifice plate are connected, and thus facilitates the fluid in the buffer zone area to diversify to culture plates.

A plurality of culture wells is formed on the culture plate with no limitation for the appearance. However, the shape of a circle or polygon is preferred, and more preferably, is hexagonal. The location of the injection ports connecting the culture wells has no limitation. Preferably, the injection ports of the culture plate are formed on the corners of the hexagon-shape culture wells, to receive the fluid from the orifice plate evenly into each culture well.

The culture wells in this micro device for cell culture of the invention achieve a very successful result by using bio-compatible material to form micro-patterning, or scaffolds can be applied to each culture well to culture cells with different characteristics.

Before using the culture wells of the invention, a matrix can be attached to facilitate cell culture.

In order to increase the quantity of cell culture, this micro device can be connected with more than one device to conduct mass cell culture at the same time and in the same environment. No rules are applied when connecting each micro device; however, serial or parallel connection is recommended.

A plurality of culture units can also be combined within one single micro device in which the quantity of cell cultured is enlarged. Each culture unit includes a orifice plate and a culture plate placed between the top plate and the bottom plate. Preferably, each cell culture unit includes a dividing plate to separate each culture unit. The aforementioned dividing plate has an outlet hole and a center slot with a plurality of orifices. Each orifice is connected with the injection ports on the culture plate of the culture unit.

This micro device performs even better when including a mechanical engineering control system and a biosensor. The mechanical engineering control system can manipulate the variety of fluids, the flow speed, the supply period, and the supply volume. Preferably, micro-patterning is formed inside each culture well. The structure of micro-patterning with at least one recess can be formed with bio-compatible materials by photosensitive procedures. Or, a pattern with at least one recess can be constructed in the culture wells by bio-compatible materials or bio-matrix, to control the growth and arrangements of cells.

The orifice plate of the invention decreases the probability of concentration variation and shear force occurring around the inlet port while the fluid flows into an culture well. The cooperation of orifices on the orifice plate and a hexagon-shape culture well achieves the best flow field effect, e.g. the shear force occurs more evenly when fluid flows from the six corners of the hexagon toward the center. Furthermore, the concentration gradient is formed within the cell culture wells by controlling the strength of inputting the fluid. The phenomenon reflects the concentration difference when a cell grows. For example, the concentration gradient of metabolism activity is different from central vein to portal vein of liver cells. The micro device for cell culture of the present invention can imitate the cell growing activity in physical environment in vitro.

The present invention also includes a fluid control system which cooperates with a micro device for cell culture including: at least one pump; at least one valve; and one control unit. The micro device for cell culture contains a top plate having at least one inlet port, a orifice plate, a culture plate, and a bottom plate. The valve of the fluid control system connects at least one fluid supply unit and an inlet port on the top plate of the micro device for cell culture. The control unit connects the pump and valve to control the incoming and outgoing fluid.

By the fluid control system of this invention, different biomoleculars and drug delivery unit can be connected and automatically controlled to initiate or stop bio signal transmission at a sandwiched time interval. Moreover, a biosensor can also be connected to conduct feedback control on the returned signal. The biological systems can imitate how it transmits the growing factor to control cell behavior, and the long-term cultured cells can be in a more dynamic and varying environment. Therefore, the restraints or changes of the related metabolism system caused by growth factor concentrations degradation or unmorally high are avoided.

The present invention also includes a cell culture system comprises the micro device as described above; a microscopy or other image capture unit drug delivery unit; a medium transfer unit; a gas or air supply unit; and a temperature control unit.

Other objects, advantages, and novel features of the invention will become more apparent from the following detailed description when taken in conjunction with the accompanying drawings.

DETAILED DESCRIPTION OF THE PREFERRED EMBODIMENT

The device in this invention has many kinds of combination as illustrated in the following.

EXAMPLE 1

Figure 1:
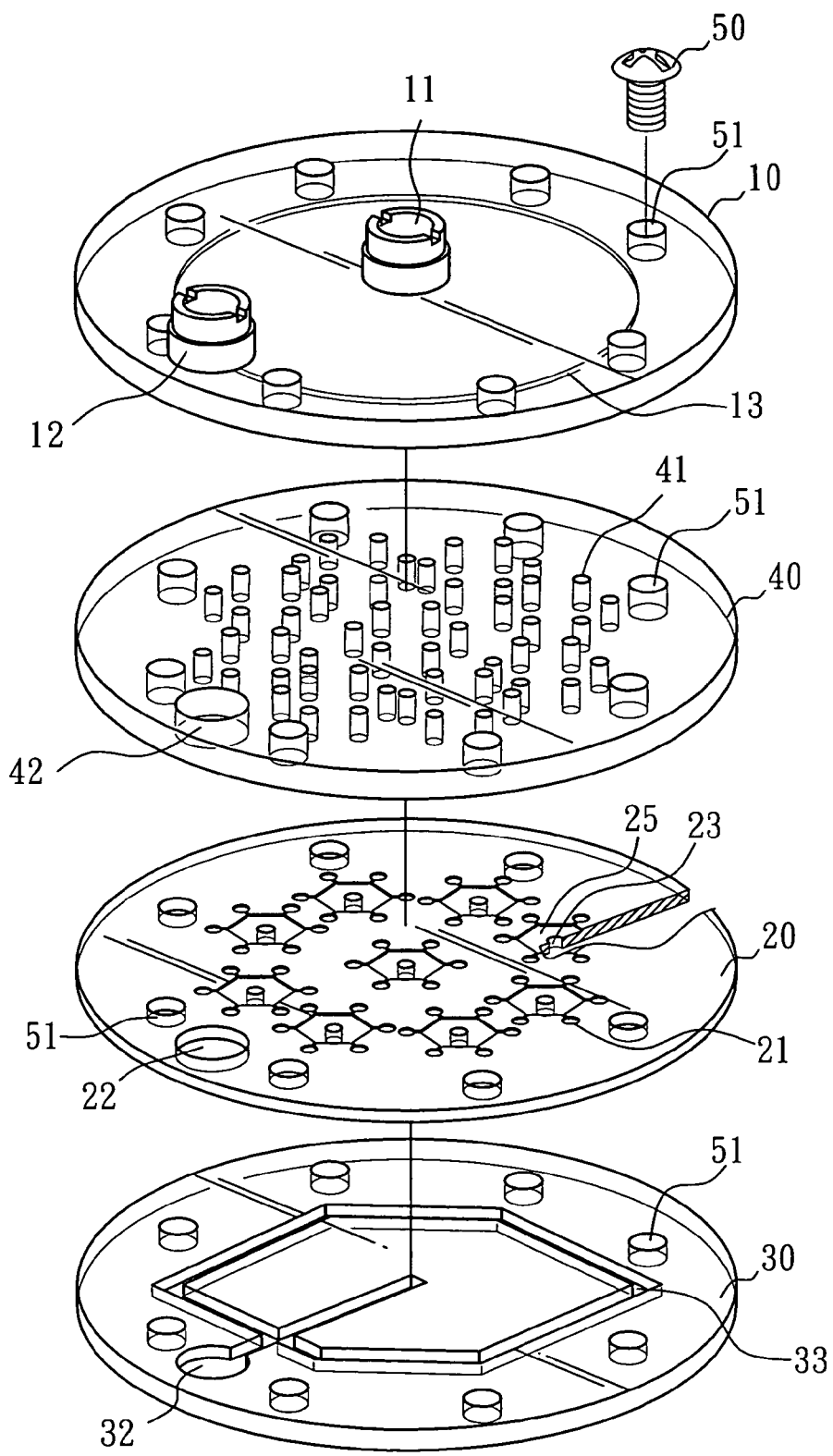
FIG. 1 is an exploded drawing of the micro device for cell culture in example 1.

FIG. 1 is a detailed diagram of the micro device for cell culture. Four components are included which are: a top plate 10, a orifice plate 40, a culture plate 20, and a bottom plate 30. Each component has a plurality of screw holes 51 in which screws 50 are used to connect each component. In this example, eight screw holes 51 are formed on each component, to tightly connect with four components by screws 50. Therefore, cells cultured in the micro device can be prevented from being contaminated through external contacts during the culturing process.

An inlet port 11, an outlet port 12, and a buffer zone 13 are formed on the surface of the top plate 10. The buffer zone 13 is formed on the surface of the top plate 10 corresponding to the orifice plate 40. When the top plate 10 and the orifice plate 40 are assembled, the buffer zone 13 is formed and provides a temporary reserve for the fluid from inlet port 11 on the top plate 10.

A plurality of orifices 41 is formed on the surface of the orifice plate 40. The orifices 41 receive the fluid from the inlet port 11 on the top plate 10, then the fluid is evenly guided to the culture plate 20 via the plurality of orifices 41. Meanwhile, an outlet port 42 is also formed on the orifice plate 40 and corresponds with the outlet port 12 of the top plate 10 to connect each other.

A plurality of culture wells 25 is formed on the surface of the culture plate 20. In the present example, nine hexagon-shape culture wells 25 are formed on the same surface. A injection port 21 is formed at each corner of the hexagon-shape culture well 25, and connects with the orifice 41 on the orifice plate 40.

At least one regulating orifice 23 is formed in each culture well 25. The opening of each regulating orifice 23 has a height difference with the bottom of the culture wells 25. The regulating orifices 23 penetrate the culture plate 20 and connect with bottom plate 30 while assembling. When the fluid surface in culture wells 25 is higher than the regulating orifices 23, excess fluid is to be removed into the bottom plate 30 by passing through regulating orifice 23. Meanwhile, an outlet port 22 is also formed on the culture plate 20 at the locations corresponding to the outlet ports 12, 42 on the top plate 10 and the orifice plate 40.

At least one collecting well 32 and one flow channel 33 are formed on the bottom plate 30. When the micro device for cell culture is assembled, the culture plate 20 is placed between the orifice plate 40 and the bottom plate 30. The flow channel 33 is linked with the regulating orifices 23, and the fluid from culture wells 25 flows along the flow channel 33 and is gathered in collecting well 32.

Figure 2:
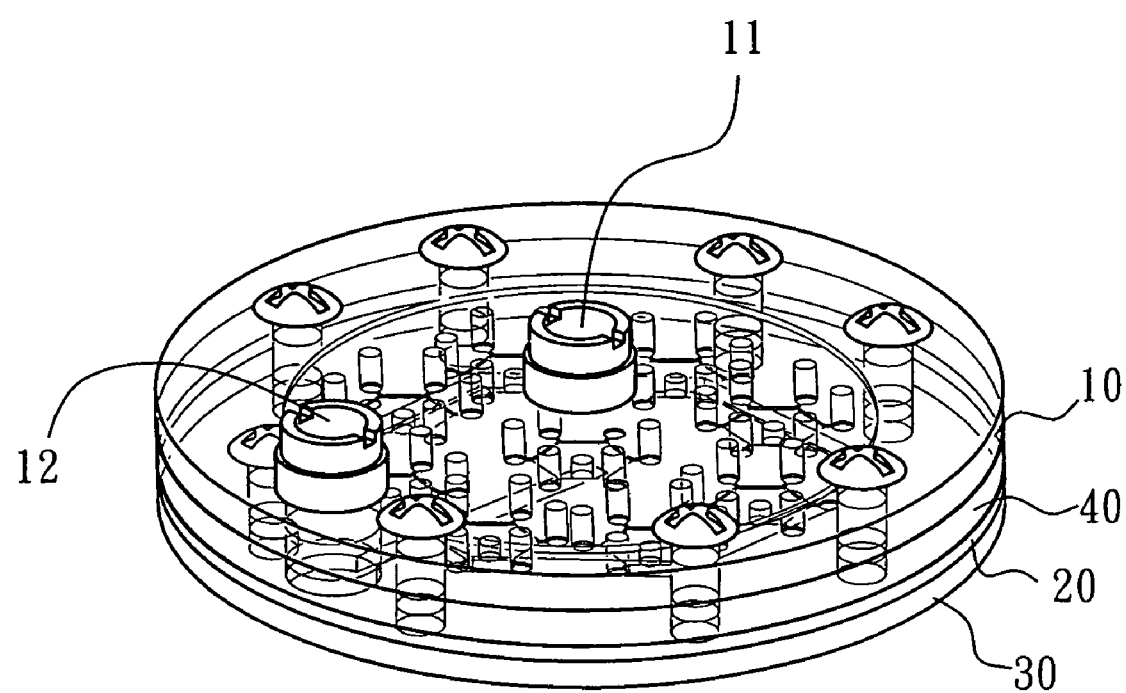
FIG. 2 is a view of the micro device for cell culture in example 2 after assembling.

When assembling, the screws are tightened in the eight screw holes 51 in the order of top plate 10, orifice plate 40, culture plate 20, and bottom plate 30; the configuration of the micro device after assembling is shown in FIG. 2. In this example, the orifice plate 40 and the bottom plate 30 are made from soft materials to ensure each component tightly abuts another after assembling. After assembly, the outlet port 12 on the top plate 10 should correspond with the outlet ports 42, 22 on the orifice plate 40 and the culture plate 20, as well as the collecting well 32 on the bottom plate 30. The excess fluid in collecting well 32 drains out from top plate 10 along outlet ports 42, 22, 12.

A connecting pipe (not shown) can be utilized to link with inlet port 11 and outlet port 12 on the top plate 10. The back-flowing fluid can be re-used by flowing into the inlet port 11 via the outlet port 12, or the excess fluid can drain out of the micro device via the outlet port 12.

In this device, the regulating orifice 23 in culture wells 25 corresponds with flow channel 33 on the bottom plate 30. Therefore, all the excess fluid from culture wells 25 can be properly collected to avoid overflow on the component and thus contamination is avoided.

EXAMPLE 2

Figure 3A:
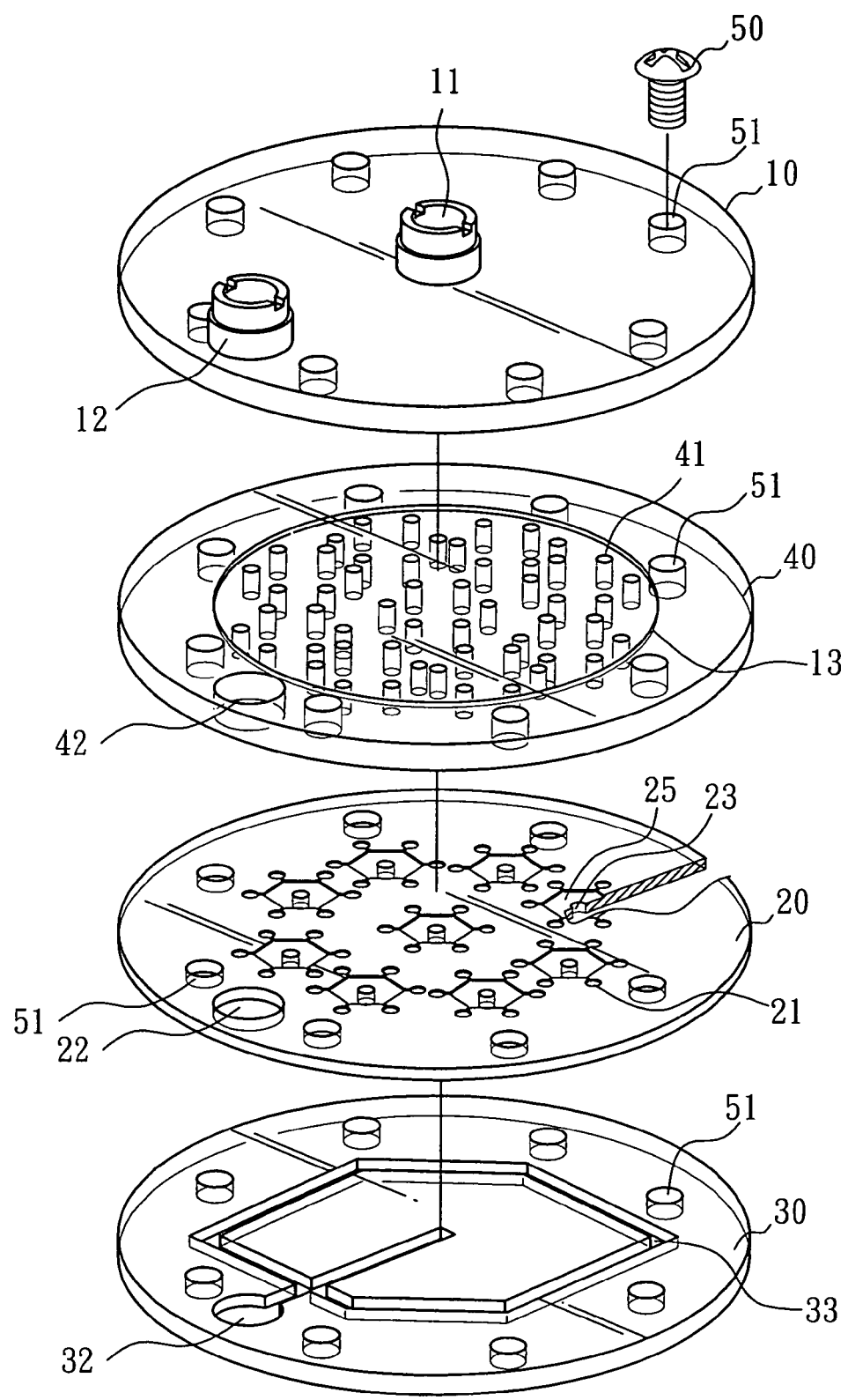
FIG. 3A is an exploded drawing of the micro device for cell culture in example 2.

The other structure of this device is as shown as in FIG. 3A. The buffer zone 13 formed on the top plate 10 can be formed on orifice plate 40 corresponding to a surface of top plate 10 instead, while the buffer zone 13 can also be formed when the top plate 10 and the orifice plate 40 are assembled.

EXAMPLE 3

Figure 3B:
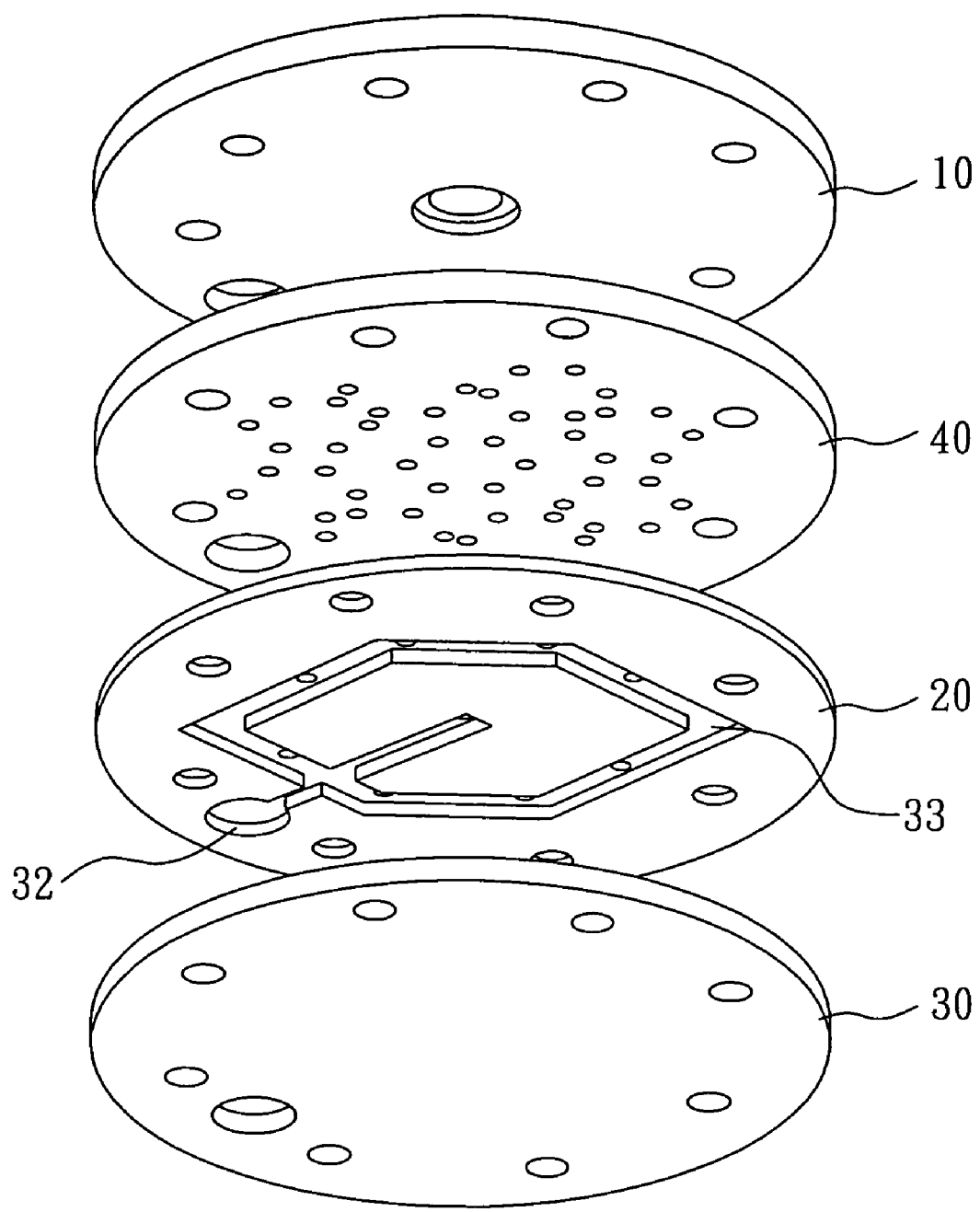
FIG. 3B is an exploded drawing of the micro device for cell culture in example 3.

As shown in FIG. 3B, the flow channel 33 and the collecting well 32 originally formed on the bottom plate 30 can also be formed on the culture plate 20 on a surface facing the bottom plate 30. The flow channel 33 and the collecting well 32 can thus be formed between the culture plate 20 and the bottom plate 30 when the micro device has been assembled.

EXAMPLE 4

Figure 3C:
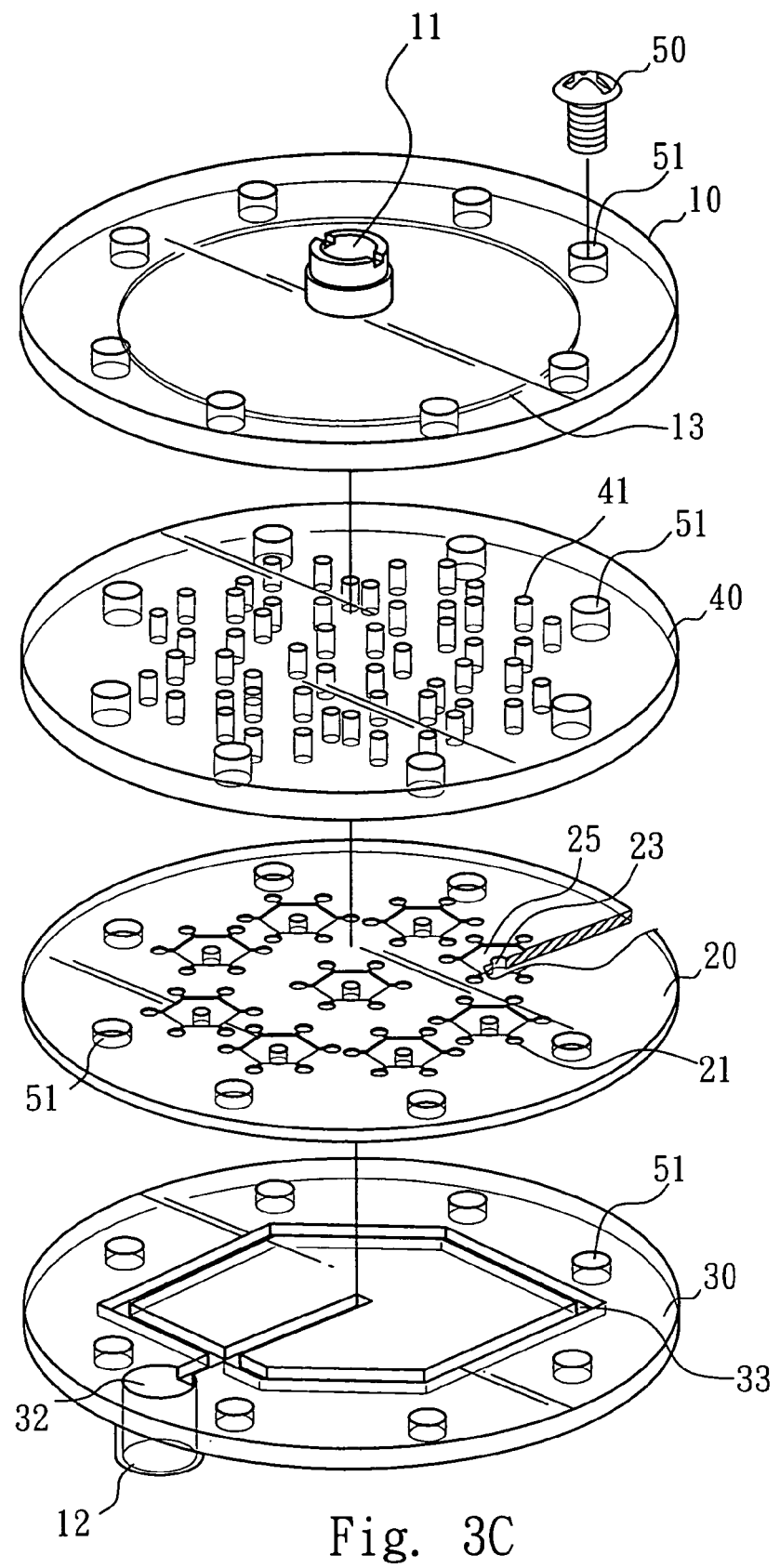
FIG. 3C is an exploded drawing of the micro device for cell culture in example 4.
Figure 3D:
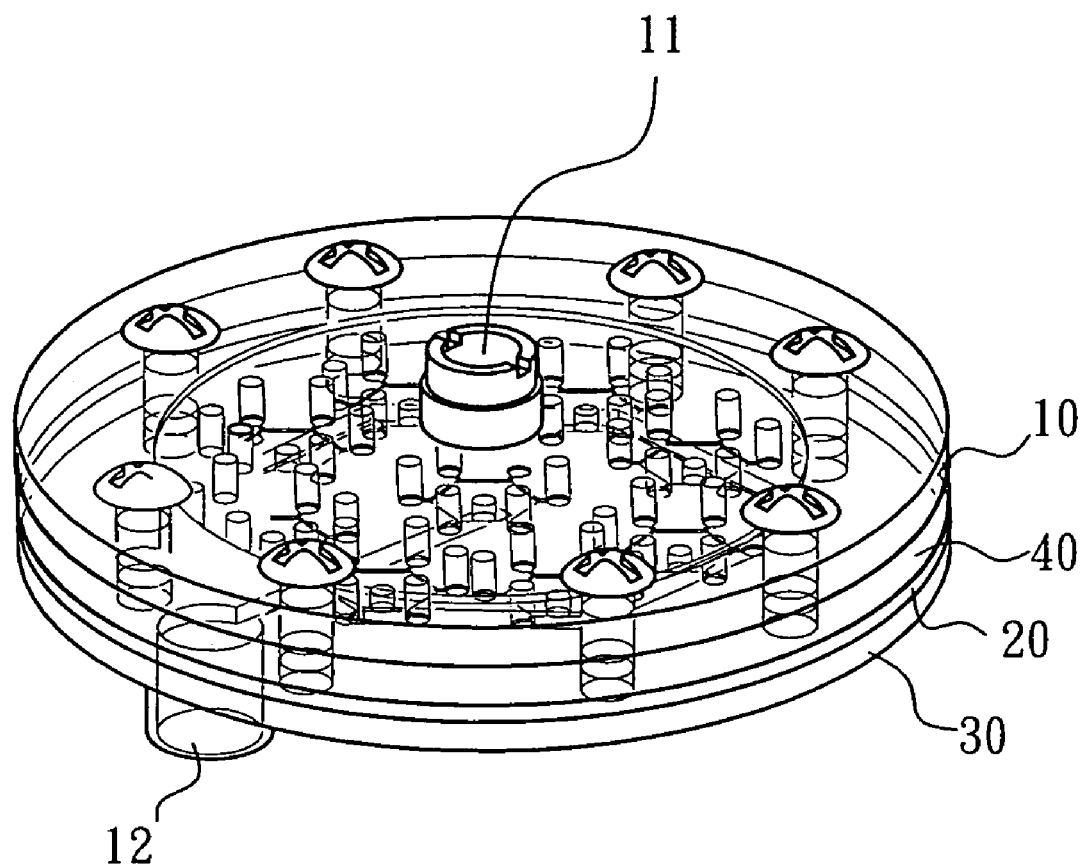
FIG. 3D is view of the micro device for cell culture after assembling in example 4.

In FIG. 3C, the collecting well 32 on the bottom plate 30 is connected with outlet port 12 directly, to drain the fluid in the collecting well 32 out of the micro device without back flow. Therefore, the outlet ports 12, 42, and 22 on the top plate 10, the orifice plate 40 and the culture plate 20 are not necessary. This type of micro device for culture cell is assembled, and shown in FIG. 3D.

EXAMPLE 5

Figure 4:
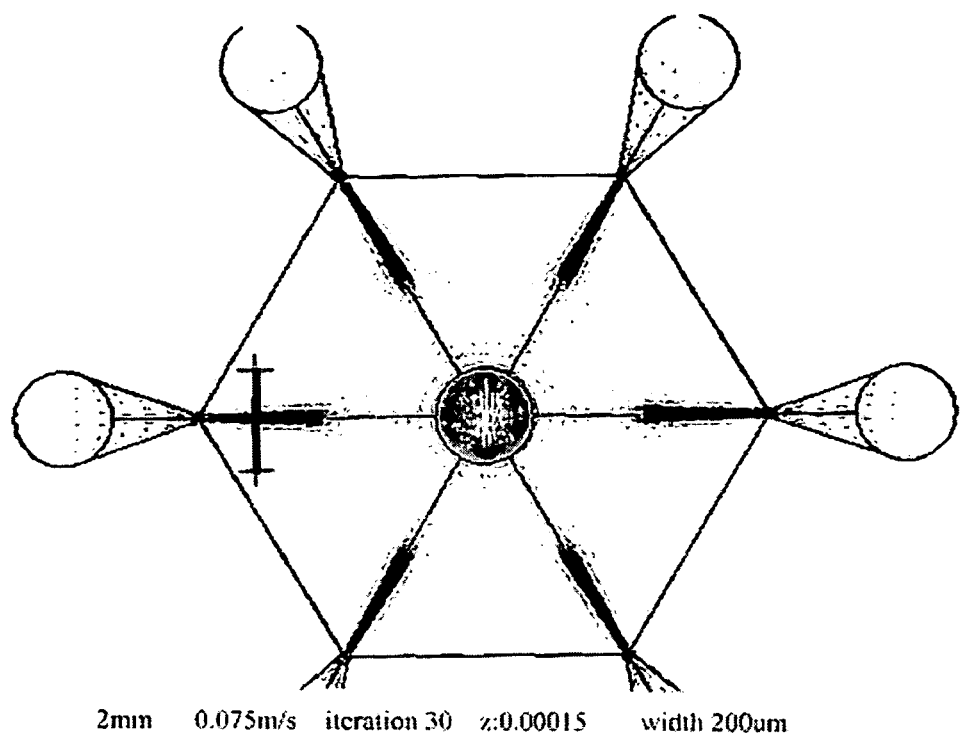
FIG. 4 is the imitating result of the fluid field in each culture well of the present micro device for cell culture.
Figure 5:
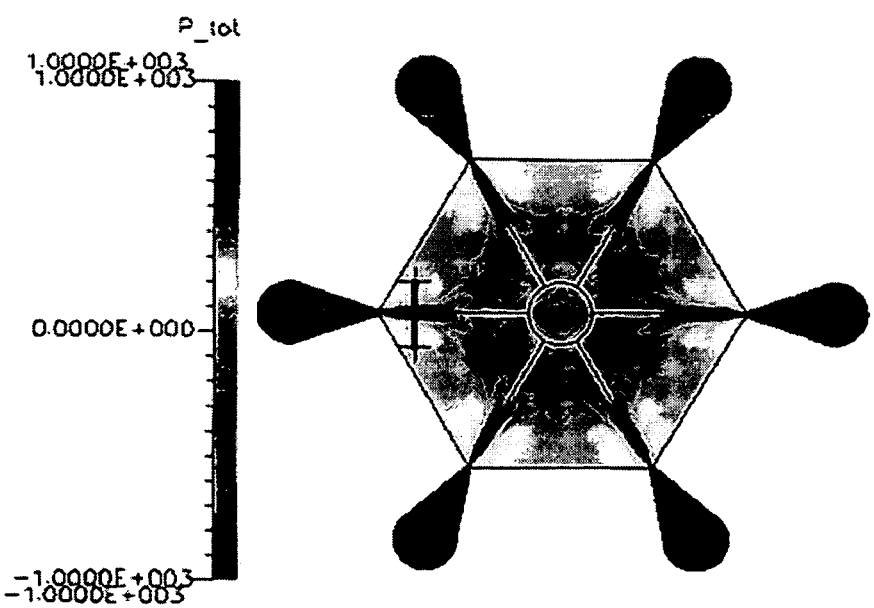
FIG. 5 is the pressure change in each culture well of the present micro device for cell culture.

By flow field research, the ability of physical environment imitation is demonstrated by the micro device for cell culture. When analyzing by computer the flow field vector of the cell culture wells, it is discovered that when inputting fluid from the comers of the hexagon-shape culture wells, the pressure on the inlet port does differ from that in the center; the concentration of fluid changes according to the pressure. That is, as shown in FIG. 4, the concentration around the inlet port is higher than that in the central position. The difference of pressure can be detected by the gradual concentration relation shown in FIG. 5. As shown in FIG. 4, the fluid flows from the comers of a hexagon toward the center at the flow rate of 0.075 m/s, the pressure change of $1000(N/m^2)$ is produced as an imitating result as shown in FIG. 5. It is observed that the device of this invention can imitate the gradient effect of molecular diffusion within an organism by concentration difference caused by pressure.

EXAMPLE 6

To perform cell culture by using the micro device of the invention, cells are loaded first. There are several methods for cell loading. For example, a biological matrix can be attached to cell culture wells 25, and then cell culture is conducted. The components shown in FIG. 1 are assembled as shown in FIG. 2. After 24 hours of cell attaching, culture media is injected into inlet port 11 for perfusion. The culture media will diversify into culture wells 25 via orifice s 41 in the orifice plate 40. When the culture wells 25 are full of culture media, the fluid will flow vertically into flow channels 33 on bottom plate 30 via regulating orifice 23 of culture wells 25, and then gather in collecting well 32.

Alternatively, after the biological matrix is attached to the culture wells 25, the micro device for cell culture is assembled. Seedling cells are perfused in the micro device. The seedling cells are circulated in the injection ports, and attached to the culture wells with the bio-matrix for propagation. Perfusion may be stopped at this time. After four to six hours, cell culture media is applied again with low flowing rate.

After the cells are implanted into the micro device, perfusion can be conducted with different flow rates and different media or solutions. After a predicted culture period, e.g. for 1 day, 3, 5, or 7 days, the cell morphology is observed with a microscope.

EXAMPLE 7

Figure 6A:
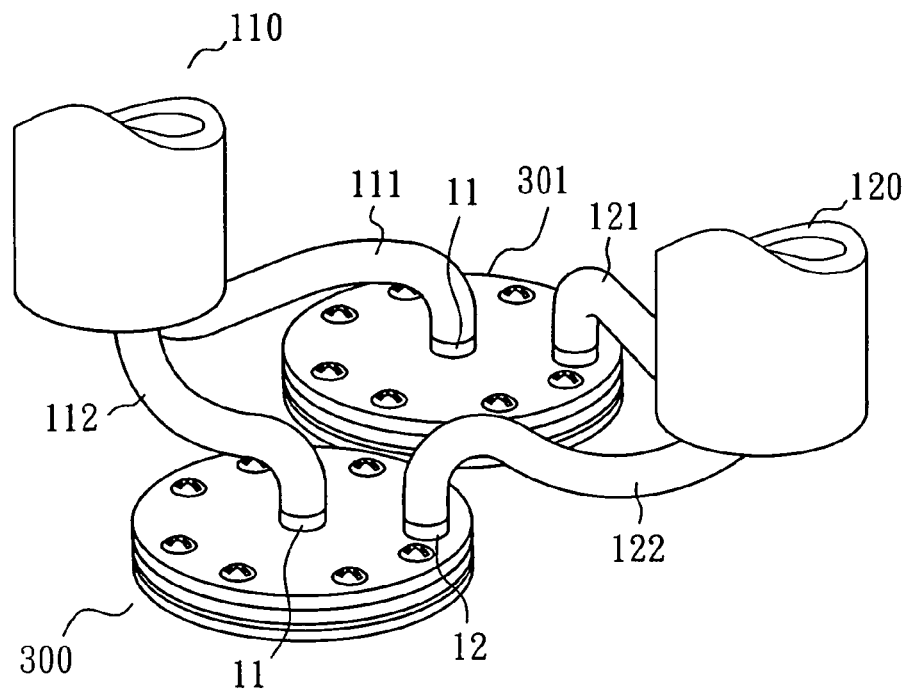
FIG. 6A illustrates the parallel connection of micro devices in example 7.
Figure 6B:
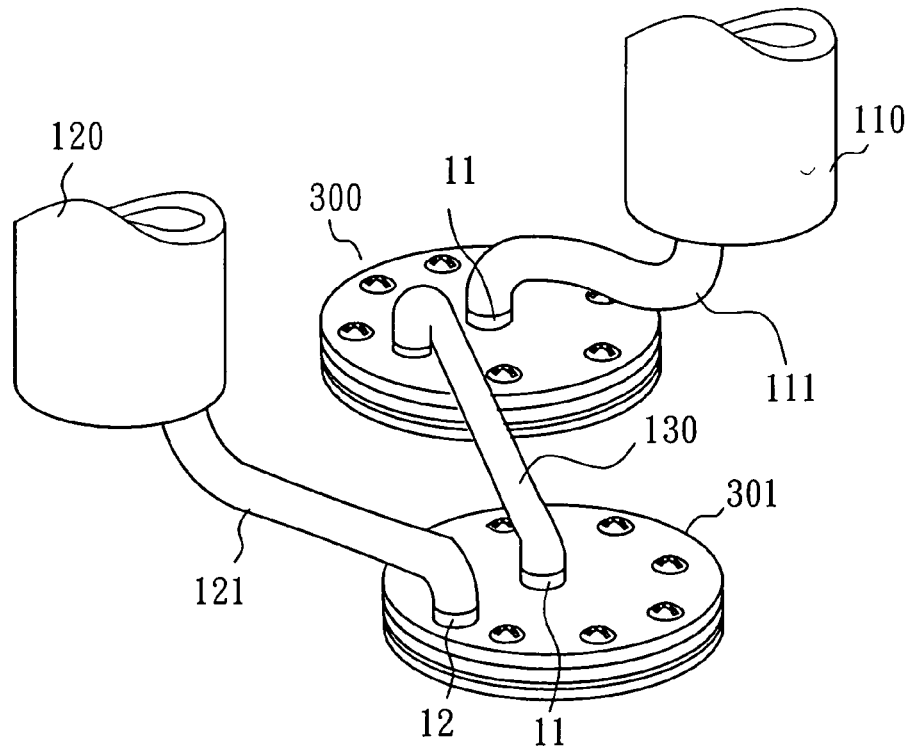
FIG. 6B illustrates the serial connection of micro devices in example 7.
Figure 6C:
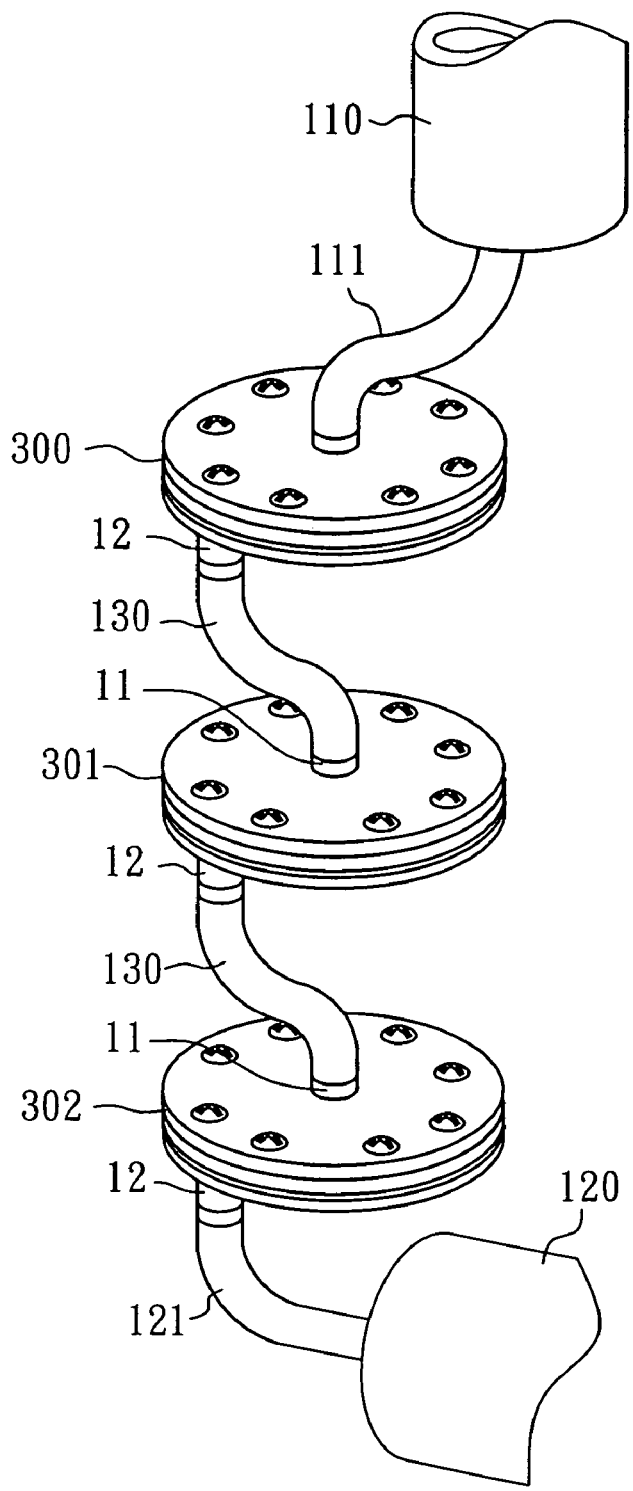
FIG. 6C illustrates another serial connection of micro devices in example 7.

More than one micro device of the invention can be connected in different ways. As shown in FIG. 6A to FIG. 6C, serial or parallel connection can be applied to connect more than two micro devices 300, 301 to perform mass production.

Parallel connection of micro devices for cell culture 300, 301 is illustrated in FIG. 6A. A fluid supply unit 110 connects branched diversion pipes 111, 112 with the inlet ports 11 on the micro devices 300 and 301. Moreover, a collecting unit 120 also includes branched diversion pipes 121, 122, and connects with outlet ports 12 on micro devices 300 and 301. By the way of parallel connection, both micro devices 300 and 301 can conduct cell culture in the same culture media at the same time.

When conducting mass production of cells, a cell culture media should be provided in micro devices 300, 301 via fluid supply unit 110. The cell culture is conducted as mentioned in example 3. When the cultured cells are collected, the collecting unit 120 connected with outlet ports 12 can be used to receive the products from independent micro devices 300, 301.

Another connection way to join more than two micro devices to perform mass production is by serial connection. As shown in FIG. 6B, the inlet port 11 on the micro device 300 is connected to a fluid supply unit 110 with a diversion pipe 111. The inlet port 12 on the same micro device 300 is connected to the inlet port 11 on the micro device 301 with an airtight connecting pipe 130. The outlet port 12 on the micro device 301 is connected with the collecting unit 120 by the diversion pipe 121.

The culture media is supplied into the micro device 300 via the fluid supply unit 110 as the culturing process mentioned in example 3. The excess culture media is injected into another serial-connected micro device 301 via the connecting pipe 130, and the cell culture is then conducted in the second micro device 301.

Alternatively, after conducting cell culture in micro device 300 for a period of time, the connecting pipe 130 is used as a route to output the proliferated cells and media to the serial-connected micro device 301. Meanwhile, a further cell culture procedure can be conducted to proliferate cells. Then, all the produced cells are gathered in the fluid collecting unit 120 via diversion pipe 121.

Furthermore, another type of serial connection can be used to connect more than two micro devices 300, 301 and 302 as shown in FIG. 6C. In this example, the outlet port 12 on top plate 10 is relocated to the bottom plate 30 and connected with the collecting well 32 on the bottom plate. Each inlet port 11 is connected with the outlet port 12 by different connecting pipe 130 on the three micro devices 300, 301 and 302 separately as shown in FIG. 6C. The inlet port 11 on the first micro device 300 is connected with a fluid supply unit 110 by the diversion pipe 111, to provide the cell culture media or other required material. Meanwhile, the outlet port 12 on the last micro device 301 is connected to the collecting unit 120 by another diversion pipe 121 to collect product.

EXAMPLE 8

The micro devices can be connected with more micro devices for mass cell culture as described in example 7. Furthermore, a single micro device for cell culture can also be expanded for mass production while economizing the use of space.

Figure 7A:
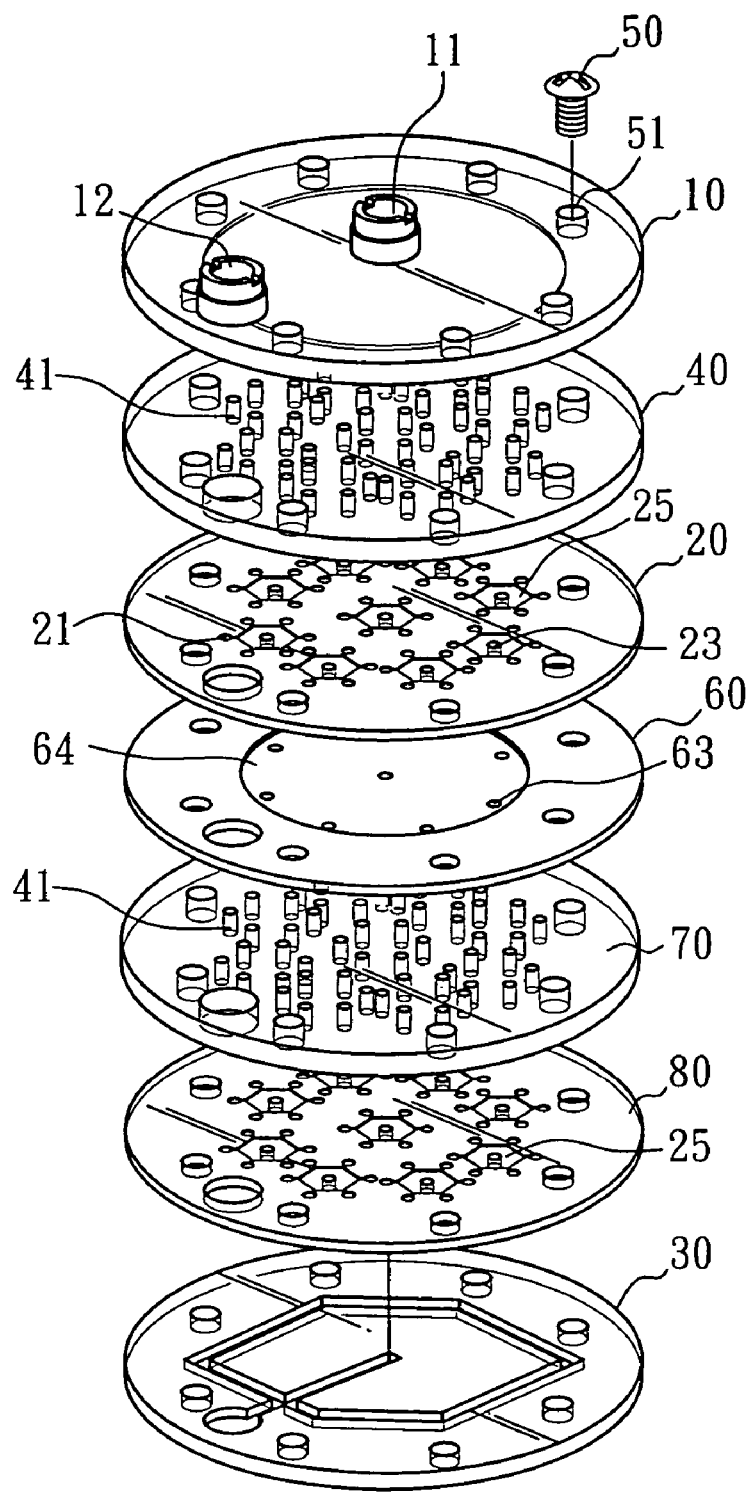
FIG. 7A shows the explosive drawing of the expanded culture unit of a micro device in example 8.

Referring to FIG. 7A, the main components shown are the same as in example 1, and include: a top plate 10, a orifice plate 40, a culture plate 20, and a bottom plate 30. However, two orifice plates 40, 70, and two culture plates 20, 80, are used in this example instead of using one plate (one orifice plate and one culture plate are one culture unit). A dividing plate 60 is placed between culture plate 20 and the orifice plate 70 for separation of two culture units.

In FIG. 7A, a buffer zone 64 on the dividing plate 60 placed between the culture plate 20 and the orifice plate 70 is formed to receive the excess culture media from culture plate 20. The excess media flows into the orifice plate 70 via the separating holes 63 formed on buffer zone 64. The orifices 41 are also used to diversify the excess culture media to each culture unit 25 on the culture plate 80, and the cell culture is also performed in the second culture unit.

If more than one dividing plate 60, orifice plate 70, and culture plate 80 are further placed in one micro device, mass cell culture can be performed by the way of serial connection. Also, each culture well in a culture unit is ensured to have the same environment for cell culture, and problems of uncertain hazard are fewer.

Figure 7B:
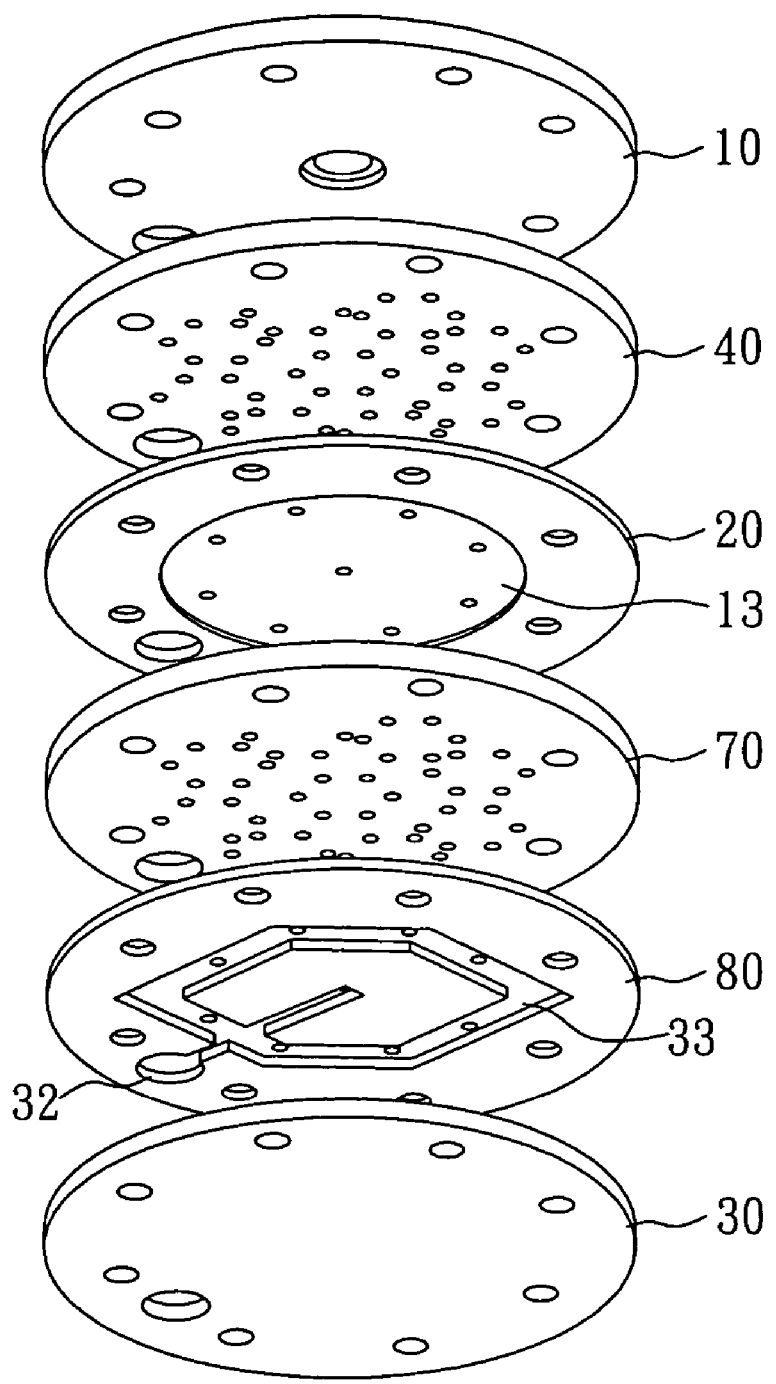
FIG. 7B shows the explosive drawing of another expanded culture unit of a micro device in example 8.

Further, another way for expanding the use of micro devices for cell culture is illustrated in FIG. 7B. A buffer zone 13 is formed on the surface which is opposite the surface with culture wells of the culture plate 20. The buffer zone 13 is formed between the culture plate 20 and the next component (e.g. the second orifice plate 70. The dividing plate is absent in the present example.), and the fluid from the culture plate 20 can be retained inside.

Also, in the present example, the flow channels 33 and the collecting well 32 are formed on one surface of the culture plate 80 instead of on the bottom plate. The flow channels 33 and the collecting well 32 are formed when the culture plate 80 and the bottom plate have been assembled.

EXAMPLE 9

Figure 8:
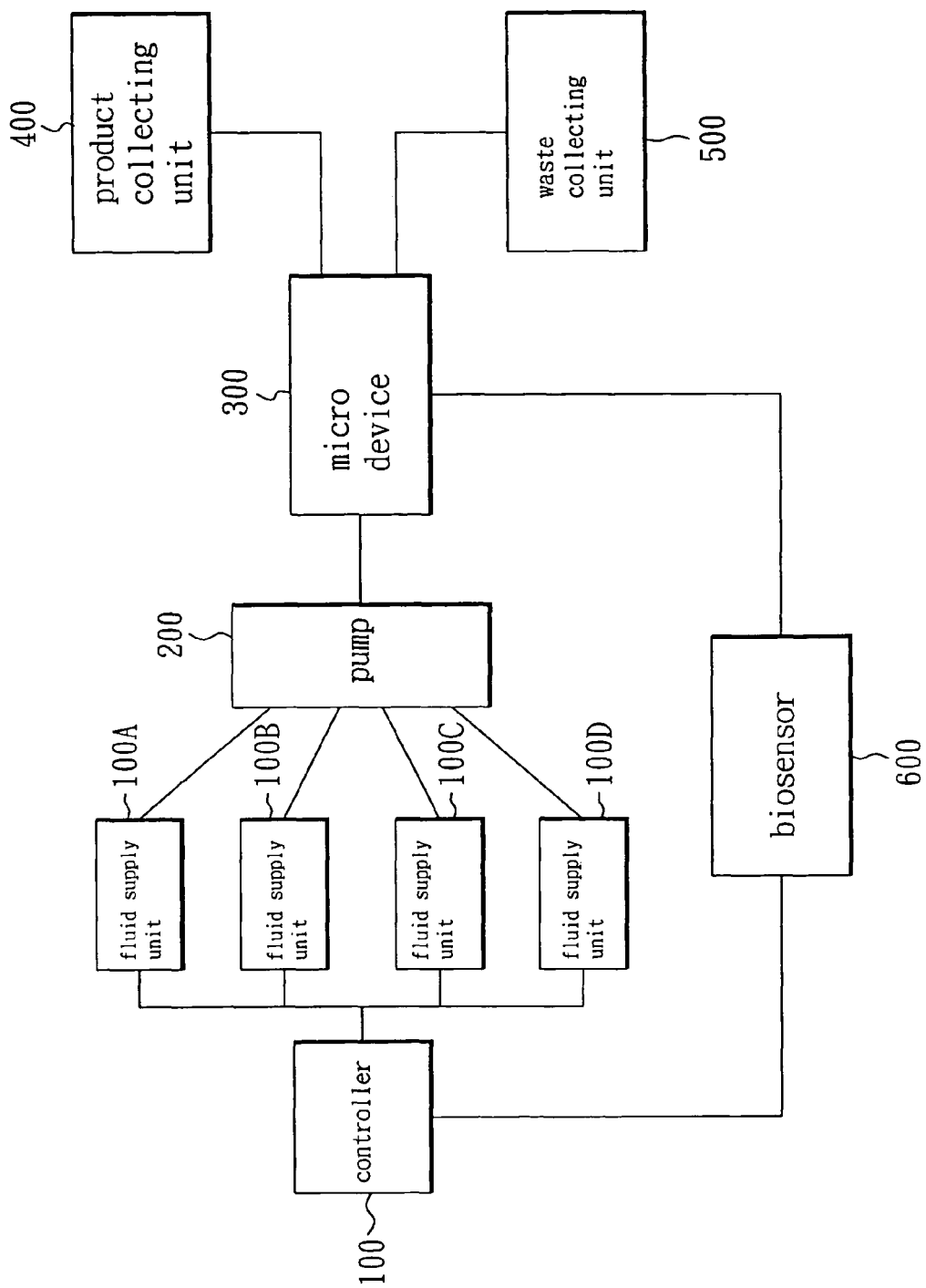
FIG. 8 shows a diagram of an automatic control system with the present micro device for cell culture.

The micro device for cell culture of the present invention can be combined to other devices for an automatic controlling system. As shown in FIG. 8, a controller 100 is connected to multiple fluid supply units 110A, 110B, 110C, 110D separately. There are four fluid supply units in the present example providing fluids such as media, growth factors or medical reagents. The four fluid supply units 110A, 110B, 110C, 110D are linked to a pump 200 individually, to pump the fluid into micro device 300. Meanwhile, the micro device 300 is connected with a product collecting unit 400 and a waste collecting unit 500. The signals generated inside the micro device 300 are detected by a biosensor 600, and fed back to controller 100, to control the variety of the fluid as well as the period or concentration factors.

Although the present invention has been explained in relation to its preferred embodiment, it is to be understood that many other possible modifications and variations can be made without departing from the spirit and scope of the invention as hereinafter claimed.

What is claimed is:

1. A micro device for cell culture, comprising:
   a top plate having an inlet port;
   an orifice plate assembled with the top plate having a plurality of orifices which are fluidly connected to and receive fluid from the inlet port of the top plate;

a culture plate having one or more culture wells and one or more injection ports; wherein the culture wells and the injection ports locate on at least one surface of the culture plate, the injection ports connect to each culture well and the orifices of the orifice plate, and at least one regulating orifice is formed inside each culture well for outputting a fluid or fluids; and a bottom plate having at least one flow channel, neighboring to one side of the culture plate, wherein the flow channel on the bottom plate is linked with the regulating orifice.

2. The micro device as claimed in claim 1, wherein the injection ports are able to form a specific fluidic pattern with gradient of nutrients, bimolecular.

3. The micro device as claimed in claim 1, wherein the culture plate is fixed between the orifice plate and the bottom plate as assembled.

4. The micro device as claimed in claim 1, wherein a buffer zone is formed between the top plate and the orifice plate as assembled, to convey the fluid flows from the top plate to culture plate.

5. The micro device as claimed in claim 4, wherein the buffer zone is formed on one side of the top plate opposite to the orifice plate, or on one side of the orifice plate opposite to the top plate.

6. The micro device as claimed in claim 1, wherein at least one collecting well is further formed on the bottom plate, and the flow channels on the bottom plate are connected to the regulating orifice of each culture well, to collect the fluid from each culture well into the collecting well.

7. A micro device for cell culture, comprising:

a top plate having an inlet port;

a orifice plate having a plurality of orifices;

a culture plate having a plurality of culture wells and a plurality of injection ports; wherein the injection ports connect to each culture well and the orifice of the orifice plate, and at least one regulating orifice is formed inside each culture well for outputting a fluid or fluids; and a bottom plate having at least one collecting well and at least one flow channel, neighboring to one side of the culture plate; the culture plate is fixed between the orifice plate and the bottom plate as assembled; and the flow channels on the bottom plate connect to the regulating orifice of each culture well, to collect the fluid from each culture well into the collecting well.

8. The micro device as claimed in claim 7, wherein the flow channels on the bottom plate are used as the collecting well.

9. The micro device as claimed in claim 7, wherein the fluid flows into the orifice plate from the inlet port of the top plate, the fluid is divided by the orifice on the orifice plate, and flows into each culture well of the culture plate, then the fluid is drained into the collecting well of the bottom plate.

10. The micro device as claimed in claim 7, wherein outlet ports are formed on the top plate, the orifice plate, and the culture plate, respectively, and the outlet ports are connected to the collecting well on the bottom plate to draw out the fluid of the collecting well from the top plate.

11. The micro device as claimed in claim 7, wherein an outlet is further formed on the bottom plate joining to the collecting well, to drain off the fluid.

12. The micro device as claimed in claim 7, wherein a buffer zone is formed between the top plate and the orifice plate as assembled, to ensure the fluid flows from the top plate.

13. The micro device as claimed in claim 7, wherein the culture wells on the culture plate are each of a circle-shape or a polygonal shape.

14. The micro device as claimed in claim 13, wherein the culture wells on the culture plate are each of a hexagon-shape.

15. The micro device as claimed in claim 14, wherein the orifices of the orifice plate are located in opposite positions of the six angles of each hexagon-shape-culture well of the culture plate.

16. The micro device as claimed in claim 7, wherein the bottom of each culture well is covered with cytoplasm.

17. The micro device as claimed in claim 7, further connecting to a mechanical engineering control system or a biosensor.

18. The micro device as claimed in claim 17, wherein the auto-control system is used to control the variety of fluids, the flow speed, the supply period, and the supply volume.

19. The micro device as claimed in claim 7, wherein micropatterns are formed in each culture well of the culture plate.

20. The micro device as claimed in claim 7, wherein scaffolds are applied to each culture well, for culturing cells with different characteristics.

21. The micro device as claimed in claim 7, wherein multiple micro devices are linked in a serial connection form, for culturing cells simultaneously.

22. The micro device as claimed in claim 7, wherein multiple micro devices are linked in a parallel connection form, for culturing cells simultaneously.

23. The micro device as claimed in claim 7, wherein the orifice plate and the culture plate are taken as a culture unit, and at least one culture unit is assembled between the top plate and the bottom plate.

24. The micro device as claimed in claim 23, wherein a dividing plate is further placed between each culture unit for separation.

25. The micro device as claimed in claim 23, wherein the dividing plate has an outlet port and a center slot, wherein a plurality of orifices is formed in the center slot, and each orifice is connected to the injection ports on the culture plate of the culture unit.

* * * * *